United States Patent
Matsuda et al.

(10) Patent No.: US 10,550,131 B2
(45) Date of Patent: *Feb. 4, 2020

(54) MERCAPTOETHYLGLYCOL URIL COMPOUND AND UTILIZATION THEREOF

(71) Applicant: SHIKOKU CHEMICALS CORPORATION, Kagawa (JP)

(72) Inventors: Akikazu Matsuda, Kagawa (JP); Naoto Okumura, Kagawa (JP); Takeshi Kumano, Kagawa (JP)

(73) Assignees: SHIKOKU CHEMICALS CORPORATION, Kagawa (JP); NAMICS CORPORATION, Niigata (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/556,450

(22) PCT Filed: Mar. 10, 2016

(86) PCT No.: PCT/JP2016/057679
§ 371 (c)(1),
(2) Date: Sep. 7, 2017

(87) PCT Pub. No.: WO2016/143879
PCT Pub. Date: Sep. 15, 2016

(65) Prior Publication Data
US 2018/0051038 A1    Feb. 22, 2018

(30) Foreign Application Priority Data
Mar. 12, 2015 (JP) .................. 2015-048959

(51) Int. Cl.
| C09J 163/00 | (2006.01) |
| C08L 63/00 | (2006.01) |
| C07D 487/04 | (2006.01) |
| C07D 519/00 | (2006.01) |
| C08G 59/66 | (2006.01) |
| C08G 59/50 | (2006.01) |
| C08K 5/17 | (2006.01) |

(52) U.S. Cl.
CPC ......... *C07D 519/00* (2013.01); *C07D 487/04* (2013.01); *C08G 59/5073* (2013.01); *C08G 59/66* (2013.01); *C08K 5/17* (2013.01)

(58) Field of Classification Search
None
See application file for complete search history.

(56) References Cited

U.S. PATENT DOCUMENTS

| 5,180,772 A | 1/1993 | Mao et al. |
| 5,430,112 A | 7/1995 | Sakata et al. |
| 10,246,550 B2 * | 4/2019 | Iwaya ..................... C08G 59/66 |
| 2014/0131618 A1 | 5/2014 | Matson |
| 2016/0040020 A1 | 2/2016 | Matson et al. |
| 2016/0040051 A1 | 2/2016 | Matson et al. |
| 2016/0289237 A1 * | 10/2016 | Kumano .............. C07D 487/04 |
| 2018/0051128 A1 * | 2/2018 | Iwaya .................... C08G 59/66 |

FOREIGN PATENT DOCUMENTS

| JP | 2-261851 | 10/1990 |
| JP | 6-211969 | 8/1994 |
| JP | 6-211970 | 8/1994 |
| JP | 7-82665 | 3/1995 |
| JP | 8-67729 | 3/1996 |
| JP | 11-171887 | 6/1999 |
| JP | 2004-126161 | 4/2004 |
| JP | 2012-153794 | 8/2012 |
| JP | 2015-59099 | 3/2015 |
| WO | 2014/078282 | 5/2014 |
| WO | 2015/080241 | 6/2015 |
| WO | 2015/141347 | 9/2015 |
| WO | 2015/163352 | 10/2015 |
| WO | 2016/027716 | 2/2016 |

OTHER PUBLICATIONS

Japanese Office Action, dated Jul. 11, 2017 in corresponding Japanese Patent Application No. 2015-048959, with English language translation.
International Search Report, dated Apr. 26, 2016 in corresponding International Application No. PCT/JP2016/057679, with English language translation.
Office Action dated Nov. 5, 2018 corresponding Chinese Patent Application No. 201680014880.5 with English translation.

* cited by examiner

*Primary Examiner* — Michael J Feely
(74) *Attorney, Agent, or Firm* — Wenderoth, Lind & Ponack, L.L.P.

(57) ABSTRACT

The present invention provides a novel mercaptoethylglycoluril compound. The present invention also provides a curing agent for an epoxy resin using the substance, an epoxy resin composition using the curing agent for an epoxy resin, and an adhesive and a sealing agent each using the epoxy resin composition.

21 Claims, 1 Drawing Sheet

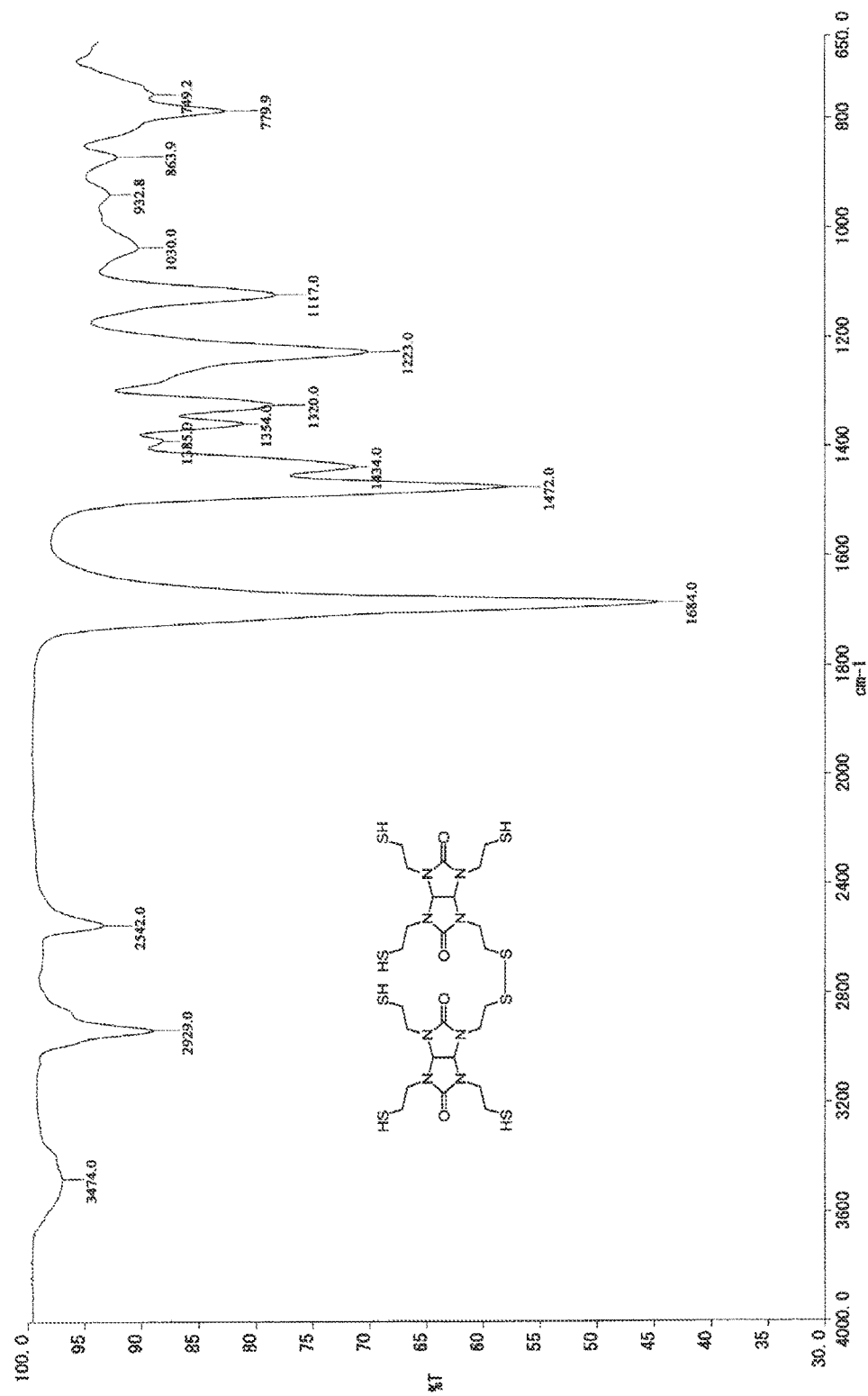

MERCAPTOETHYLGLYCOL URIL COMPOUND AND UTILIZATION THEREOF

TECHNICAL FIELD

The present invention relates to a mercaptoethylglycoluril compound and utilization thereof, and more particularly, it relates to a novel glycoluril compound classified into a thiol system, a curing agent for an epoxy resin using the substance, an epoxy resin composition using the curing agent for an epoxy resin, and an adhesive and a sealing agent each using the epoxy resin composition.

BACKGROUND ART

The glycoluril compound is a heterocyclic compound having four urea nitrogens in the ring structure thereof, and is widely used as a raw material in the production of various substances and a component of drugs in various applications, by utilizing the reactivity of the urea nitrogen.

For example, it is known that the glycoluril compound is allowed to react with an aldehyde such as dimethoxyethanal to produce an amino plastic resin and the resultant is used as a crosslinking agent for cellulose (see Patent Document 1).

It is also known that an emulsion containing a copolymer of vinyl acetate, ethylene and a self-crosslinkable monomer, and a tetramethylol glycoluril compound is used as a binder for a non-woven fabric (see Patent Document 2).

It is further known to use the compound as a crosslinking agent for fixing a polyhexamethylene biguanide compound, which is a water-soluble polymer antimicrobial agent, to a fiber (see Patent Document 3).

Compounds having a plurality of high-reactive allyl groups in the molecule, for example, triallylisocyanurate, are widely employed as a crosslinking agent for synthetic resin or synthetic rubber. Tetraallylglycoluril compounds, which function similar to the triallylisocyanurate, are also known (see Patent Document 4).

On the other hand, compounds having a plurality of thiol groups in the molecule are also well-known as a curing agent for an epoxy resin. For example, an epoxy resin composition containing a polythiol compound used as a curing agent and a reaction product of an amine with an epoxy compound as a curing accelerator is proposed. It is said that the epoxy resin composition has a long working life and is quickly cured at a relatively low temperature (see Patent Document 5).

An epoxy resin composition containing, as a curing accelerator, a reaction product of an isocyanate compound with a compound having at least one primary and/or secondary amino group in the molecule is also proposed. It is said that the epoxy resin composition also has a long working life and is excellent in curability (see Patent Document 6).

In addition, tris(3-mercaptopropyl)isocyanurate, which is also called trithiol isocyanurate, is proposed as a curing agent capable of providing a cured product of epoxy resin excellent in water resistance, because it has no ester group in the molecule (see Patent Document 7).

PRIOR ART DOCUMENT

Patent Document

Patent Document 1: JP-A-H08-67729
Patent Document 2: JP-A-H02-261851
Patent Document 3: JP-A-H07-82665
Patent Document 4: JP-A-H11-171887
Patent Document 5: JP-A-H06-211969
Patent Document 6: JP-A-H06-211970
Patent Document 7: JP-A-2012-153794

SUMMARY OF THE INVENTION

Problems that the Invention is to Solve

In addition, compounds in which N-position of a glycoluril compound is substituted with a mercaptoalkyl group are known, and among them, a glycoluril compound having a mercaptoethyl group functions as an excellent curing agent for an epoxy resin which achieves high moisture proof reliability (Japanese Patent Application No. 2013-193567, JP-A-2015-059099).

However, since this glycoluril compound is solid at ordinary temperature, crystals are easily precipitated in the formulation with an epoxy resin so that there is a problem in that the composition becomes non-uniform.

The present invention has been made in view of such circumstances, and an object thereof is to provide a novel mercaptoethylglycoluril compound, a curing agent for an epoxy resin using the substance, an epoxy resin composition using the curing agent for an epoxy resin, and an adhesive and a sealing agent each using the epoxy resin composition.

Means for Solving the Problems

As a result of the intensive investigations to solve the problems described above, the present inventors have discovered and synthesized a mercaptoethylglycoluril compound having a disulfide bond (—S—S—) and found that the intended object can be attained by incorporating the compound into a monomer of mercaptoethylglycoluril compound, to thereby complete the present invention.

That is, a first invention is a mercaptoethylglycoluril compound represented by chemical formula (I).

[Chem. 1]

$$\text{(I)}$$

(structure showing two fused bicyclic glycoluril units, each bearing HS-CH$_2$CH$_2$- groups on the four N positions and C=O groups, linked via an —S—S— bridge between two of the mercaptoethyl substituents)

A second invention is a curing agent for an epoxy resin containing a mercaptoethylglycoluril compound represented by chemical formula (II), and as an oligomer having a structure represented by chemical formula (III), at least the mercaptoethylglycoluril compound of the first invention.

[Chem. 2]

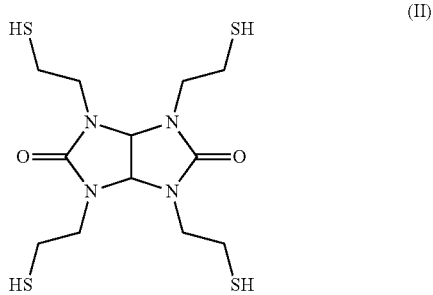

(II)

[Chem. 3]

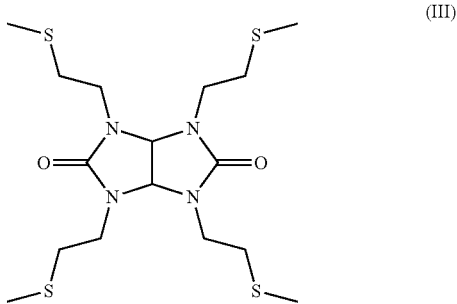

(III)

A third invention is the curing agent for an epoxy resin of the second invention, in which a ratio of a content of the oligomer having the structure represented by chemical formula (III) with respect to a content of the mercaptoethylglycoluril compound represented by chemical formula (II) is from 1 to 20% by weight.

A fourth invention is an epoxy resin composition containing the curing agent for an epoxy resin of the second invention or the third invention.

A fifth invention is the epoxy resin composition of the fourth invention, which contains an amine as a curing accelerator.

A sixth invention is the epoxy resin composition of the fourth invention, which contains a reaction product of an amine and an epoxy resin as a curing accelerator.

A seventh invention is the epoxy resin composition of the fourth invention, which contains a reaction product of an isocyanate compound and a compound having an amino group, as a curing accelerator.

An eighth invention is an adhesive, which contains the epoxy resin composition of any one of the fourth invention to the seventh invention as a component.

A ninth invention is a sealing agent, which contains the epoxy resin composition of any one of the fourth invention to the seventh invention as a component.

Advantageous Effect of the Invention

By incorporating the mercaptoethylglycoluril compound represented by chemical formula (I), which is an oligomer, into the mercaptoethylglycoluril compound represented by chemical formula (II), which is a monomer, the mercaptoethylglycoluril compound represented by chemical formula (II), which is originally solid, becomes able to be liquefied (suppress crystallization) so that the mercaptoethylglycoluril compound can be used as a liquid curing agent for an epoxy resin.

Therefore, according to the present invention, homogenization of the epoxy resin composition is assured, and by using such an epoxy resin composition as a component, an adhesive and a sealing agent each having good hydrolysis resistance and excellent in strength, heat resistance, moisture resistance and the like can be obtained.

BRIEF DESCRIPTION OF THE DRAWING

FIG. 1 is an IR spectrum chart of the purified product obtained in Example 1.

MODE FOR CARRYING OUT THE INVENTION

The present invention will be described in detail hereinafter.

In the present specification, a percentage based on weight (% by weight) has the same meaning as a percentage based on mass (% by mass). In addition, a part based on weight (part by weight) has the same meaning as a part based on mass (part by mass).

The mercaptoethylglycoluril compound represented by chemical formula (I) according to the present invention is a novel substance having a disulfide bond and a structure represented by chemical formula (III), and belongs to a multimer which is referred to as a so-called oligomer.

A chemical name of the substance is 1,1'-dithio-bisethanediyl)-bis[3,4,6-tris(2-mercaptoethyl)glycoluril].

This substance is produced together with a mercaptoethylglycoluril compound represented by chemical formula (II) (chemical name: 1,3,4,6-tetrkis(2-mercaptoethyl) glycoluril), oligomers exemplified by chemical formula (VI) to chemical formula (IX) described below and the like, by allowing to react a hydroxyethylglycoluril compound represented by chemical formula (IV) with thionyl chloride, if desired, in an appropriate solvent, to thereby obtain a chloroethylglycoluril compound represented by chemical formula (V), subsequently allowing to react the resultant with thiourea, if desired, in an appropriate solvent, followed by being subjected to hydrolysis treatment under basic conditions and then being subjected to neutralization treatment with an acid (see Reaction scheme (A)).

Reaction scheme (A)

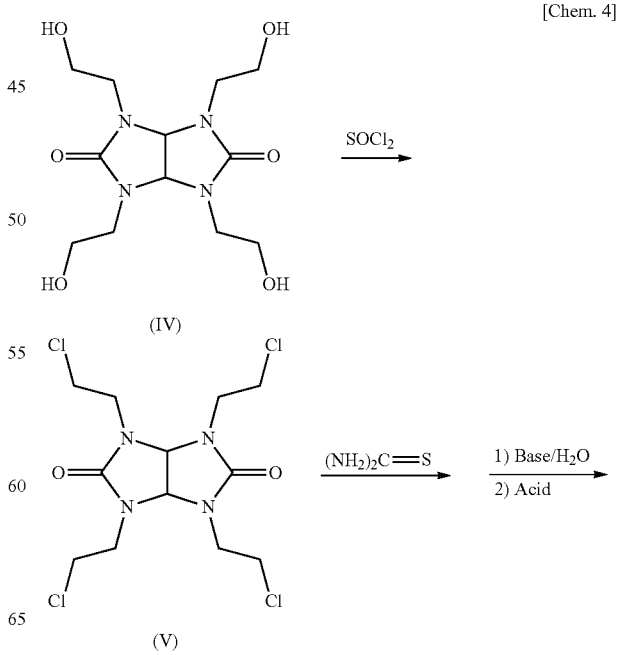

[Chem. 4]

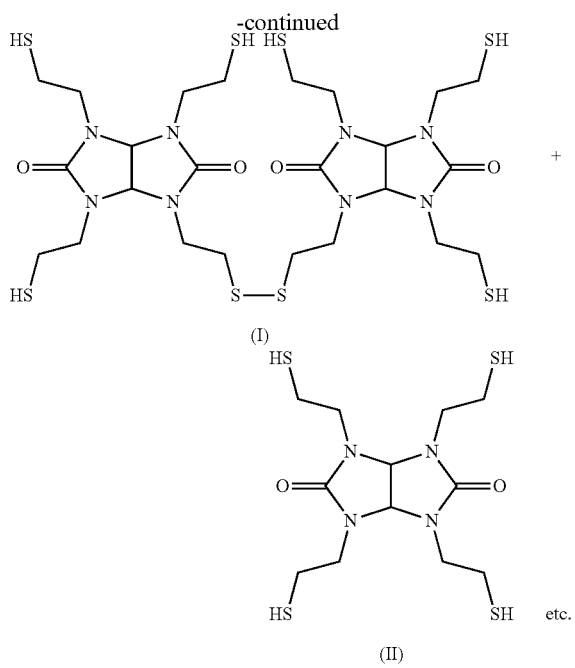

In the reaction of the hydroxyethylglycoluril compound with thionyl chloride described above, thionyl chloride is generally used in a ratio of from 1.0 to 10.0 equivalents, preferably used in a ratio of from 1.0 to 3.0 equivalents, with respect to the hydroxy group contained in the hydroxyethylglycoluril compound.

The solvent which may be used in the reaction of the hydroxyethylglycoluril compound with thionyl chloride is not particularly limited as long as it does not inhibit the reaction. Examples thereof include aliphatic hydrocarbons such as hexane and heptane, ketones such as acetone and 2-butanone, esters such as ethyl acetate and butyl acetate, aromatic hydrocarbons such as benzene, toluene and xylene, halogenated hydrocarbons such as methylene chloride, chloroform, carbon tetrachloride, chlorotrifluoromethane, dichloroethane, chlorobenzene, and dichlorobenzene, ethers such as diethyl ether, diisopropyl ether, tetrahydrofuran, dioxane, dimethoxyethane, and diethyleneglycol dimethyl ether, amides such as formamide, N,N-dimethylformamide, N,N-dimethylacetamide, N-methyl-2-pyrrolidone, and hexamethylphosphorotriamide, and sulfoxides such as dimethyl sulfoxide. These may be used in combination.

The reaction temperature of the hydroxyethylglycoluril compound with thionyl chloride is generally set in a range of from −10 to 150° C., and preferably set in a range of from 0 to 100° C.

The reaction time may be appropriately determined depending on the reaction temperature, and generally, it is set in a range of from 1 to 24 hours, and preferably set in a range of from 1 to 6 hours.

After completion of the reaction of the hydroxyethylglycoluril compound with thionyl chloride, excessive thionyl chloride and solvent may be distilled away from the reaction mixture (reaction solution) obtained, and then the reaction product obtained as a residue may be allowed to react with thiourea, if desired, with using an appropriate solvent. Or after completion of the reaction of the hydroxyethylglycoluril compound with thionyl chloride, the reaction mixture obtained as it is may be allowed to react with thiourea, if desired, with adding an appropriate solvent.

Thiourea is used in a ratio of from 1.0 to 10 equivalents and preferably used in a ratio of from 1.0 to 4.0 equivalents, with respect to the hydroxy group contained in the hydroxyethylglycoluril compound.

The solvent, which may be used in the case of allowing the reaction product obtained by the reaction of the hydroxyethylglycoluril compound and thionyl chloride to react with thiourea, is not particularly limited as long as it does not inhibit the reaction. It may be the same as the solvent which may be used in the reaction of the hydroxyethylglycoluril compound and thionyl chloride.

The temperature at which the reaction product obtained by the reaction of the hydroxyethylglycoluril compound and thionyl chloride is allowed to react with thiourea is generally set in a range of from 0 to 150° C., and preferably set in a range of from 50° C. to 120° C.

The reaction time may be appropriately determined depending on the reaction temperature, and it is generally set in a range of from 1 to 36 hours, and preferably set in a range of from 1 to 12 hours.

The reaction mixture obtained after completion of the reaction with thiourea is subjected to hydrolysis treatment with a basic compound and then subjected to neutralization with an acid, thereby obtaining a mixture of the mercaptoethylglycoluril compound represented by chemical formula (I) (oligomer) according to the present invention, the mercaptoethylglycoluril compound represented by chemical formula (II), and the oligomers exemplified by chemical formula (VI) to chemical formula (IX) described below.

Subsequently, by washing with water or an organic solvent, active carbon treatment or the like, the mercaptoethylglycoluril compound according to the present invention can be separated and purified.

Examples of the basic compound used in the hydrolysis treatment described above include hydroxides such as sodium hydroxide and potassium hydroxide, carbonates such as sodium carbonate and potassium carbonate, and amines such as ammonia, methylamine and ethylamine.

The basic compound is used in a ratio of from 1.0 to 10 equivalents, and preferably in a ratio of from 1.0 to 4.0 equivalents, with respect to the hydroxy group contained in the hydroxyethylglycoluril compound.

The solvent used in the hydrolysis treatment is not particularly limited as long as it does not inhibit the reaction. It may be the same as the solvent which may be used in the case of allowing the reaction product obtained by the reaction of the hydroxyethylglycoluril compound and thionyl chloride to react with thiourea.

The temperature of the hydrolysis treatment is generally set in a range of from 0 to 150° C., and preferably set in a range of from 50 to 120° C.

The reaction time may be appropriately determined depending on the reaction temperature set, and it is generally set in a range of from 1 to 24 hours, and preferably set in a range of from 3 to 12 hours.

Examples of the acid used in the neutralization treatment after the hydrolysis treatment includes hydrochloric acid, sulfuric acid, phosphoric acid, and the like.

Incorporation of the oligomer including the mercaptoethylglycoluril compound represented by chemical formula (I), that is, the oligomer having two or more structures represented by chemical formula (III), into the mercaptoethylglycoluril compound represented by chemical formula (II) can prevent the mercaptoethylglycoluril compound represented by chemical formula (II), which is originally solid, from crystallization.

The content of the oligomer described above in the mercaptoethylglycoluril compound represented by chemical formula (II) is preferably in a ratio of from 1 to 20% by weight with respect to the weight of the mercaptoethylglycoluril compound. The mercaptoethylglycoluril compound containing the oligomer within this ratio is suitably used as a liquid curing agent for an epoxy resin.

Examples of the oligomer other than the mercaptoethylglycoluril compound represented by chemical formula (I) include a trimer represented by chemical formula (VI) in which n is 1 or represented by chemical formula (VII), a tetramer represented by chemical formula (VI) in which n is 2 or represented by chemical formula (VIII), and a pentamer represented by chemical formula (VI) in which n is 3 or represented by chemical formula (IX).

[Chem. 5]

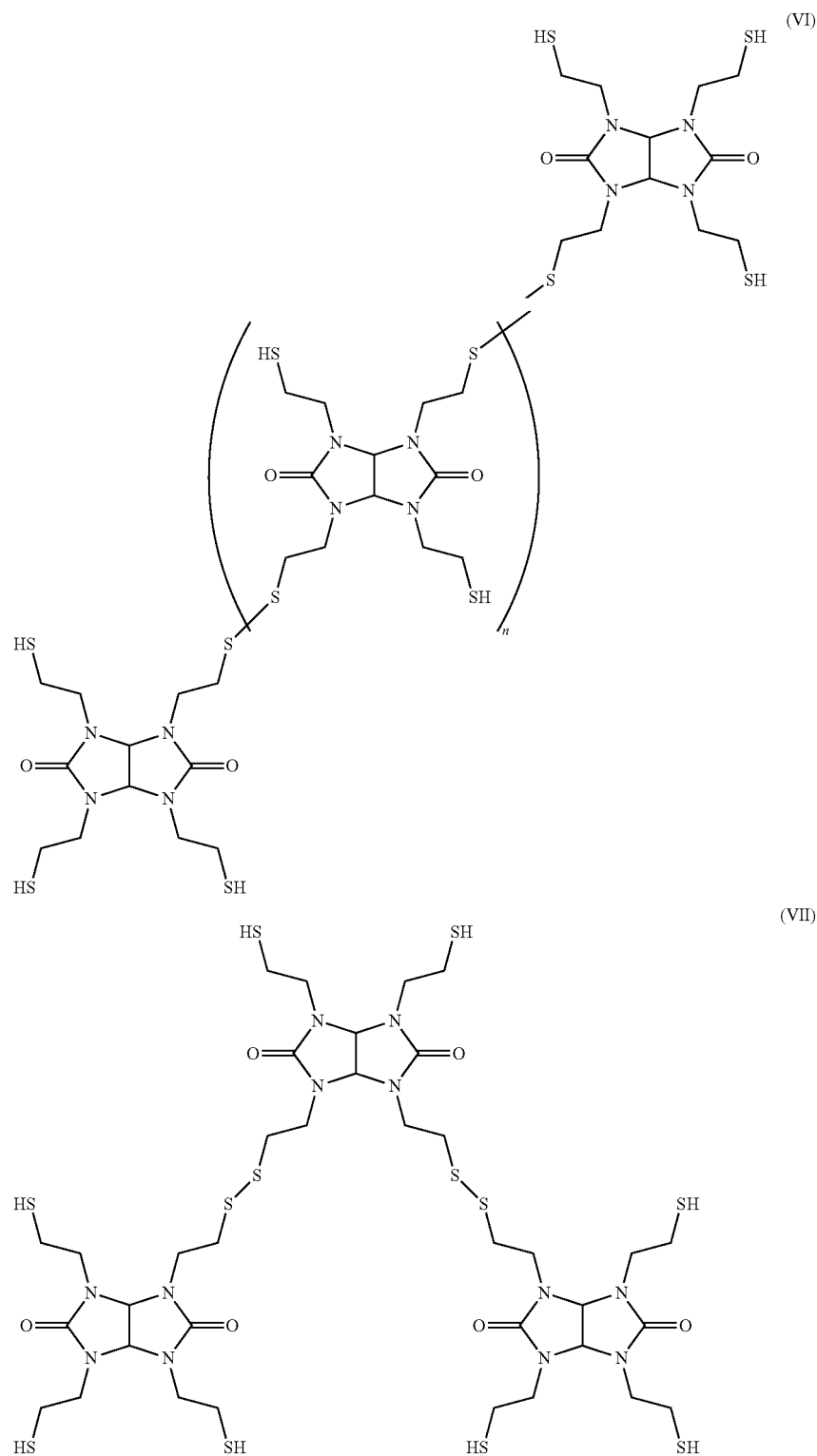

[Chem. 6]

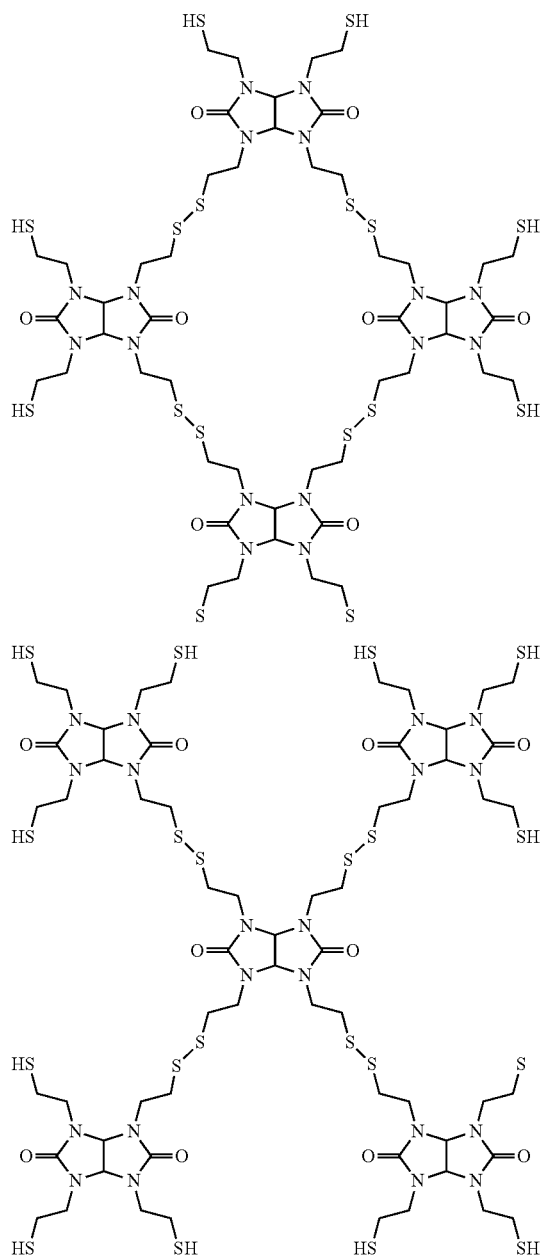

(VIII)

(IX)

The epoxy resin composition according to the present invention contains an epoxy resin as a base, and the mercaptoethylglycoluril compound represented by chemical formula (II) and as the oligomer having a structure represented by chemical formula (III), at least the mercaptoethylglycoluril compound represented by chemical formula (I), as curing agents.

In addition, the epoxy resin composition according to the present invention may contain a curing accelerator.

The curing accelerator includes (A) amines, (B) reaction products of an amine and an epoxy resin and (C) reaction products of an isocyanate compound and a compound having an amino group, and these may be used in combination.

In the present invention, the epoxy resin refers to an epoxy compound having two or more epoxy groups in one molecule on an average. As conventionally known, examples of such an epoxy resin includes: polyglycidyl ethers obtained by reacting a polyhydric phenol such as bisphenol A, bisphenol F, bisphenol AD, catechol, or resorcinol, or a polyhydric alcohol such as glycerol or polyethylene glycol with epichlorohydrin; glycidyl ether esters obtained by reacting a hydroxycarboxylic acid such as p-hydroxybenzoic acid or β-hydroxynaphthoic acid with epichlorohydrin; polyglycidyl esters obtained by reacting a polycarboxylic acid such as phthalic acid or terephthalic acid with epichlorohydrin; epoxidized phenol novolak resins; epoxidized cresol novolak resins; epoxidized polyolefins; cyclic aliphatic epoxy resins; and urethane-modified epoxy resins. These may be used in combination.

Moreover, as the epoxy resin, a glycidylglycoluril compound having two or more epoxy groups in the molecule may be used. Examples of such a glycidylglycoluril compound include:
1,3-diglycidylglycoluril,
1,4-diglycidylglycoluril,
1,6-diglycidylglycoluril,
1,3,4-triglycidylglycoluril,
1,3,4,6-tetraglycidylglycoluril,
1,3-diglycidyl-3a-methylglycoluril,
1,4-diglycidyl-3a-methylglycoluril,
1,6-diglycidyl-3a-methylglycoluril,
1,3,4-triglycidyl-3a-methylglycoluril,
1,3,4,6-tetraglycidyl-3a-methylglycoluril,
1,3-diglycidyl-3a,6a-dimethylglycoluril,
1,4-diglycidyl-3a,6a-dimethylglycoluril,
1,6-diglycidyl-3a,6a-dimethylglycoluril,
1,3,4-triglycidyl-3a,6a-dimethylglycoluril,
1,3,4,6-tetraglycidyl-3a,6a-dimethylglycoluril,
1,3-diglycidyl-3a,6a-diphenylglycoluril,
1,4-diglycidyl-3a,6a-diphenylglycoluril,
1,6-diglycidyl-3a,6a-diphenylglycoluril,
1,3,4-triglycidyl-3a,6a-diphenylglycoluril, and
1,3,4,6-tetraglycidyl-3a,6a-diphenylglycoluril.

These may be used in combination.

<(A) Regarding Use of Amine as Curing Accelerator>

The amines may be one having one or more active hydrogen atoms capable of performing an addition reaction with an epoxy group in the molecule and having at least one amino group selected from a primary amino group, a secondary amino group and a tertiary amino group in the molecule, as conventionally known.

Examples of the amines include aliphatic amines such as diethylenetriamine, triethylenetetramine, n-propylamine, 2-hydroxyethylaminopropylamine, cyclohexylamine, and 4,4'-diaminodicyclohexylmethane, aromatic amines such as 4,4'-diaminodiphenylmethane and o-methylaniline, nitrogen-containing heterocyclic compounds such as 2-ethyl-4-methylimidazole, 2-methylimidazole, 2-ethyl-4-methylimidazoline, 2,4-dimethylimidazoline, piperidine, and piperazine, and the like. These may be used in combination.

<(B) Regarding Use of Reaction Product of Amine and Epoxy Resin as Curing Accelerator>

The reaction products of an amine and an epoxy resin is solid and insoluble in the epoxy resin at room temperature but is solubilized by heating to function as the curing accelerator. Therefore, it is also called as a latent curing accelerator.

Hereinafter, the curing accelerator containing the reaction product of an amine and an epoxy resin as a component is referred to as the latent curing accelerator. The latent curing accelerator may be subjected to a surface treatment with an isocyanate compound or an acidic compound.

Examples of the epoxy resin used in the production of the latent curing accelerator include: polyglycidyl ethers obtained by reacting a polyhydric phenol such as bisphenol A, bisphenol F, catechol or resorcinol, or a polyhydric alcohol such as glycerol or polyethylene glycol with epichlorohydrin; glycidyl ether esters obtained by reacting a hydroxycarboxylic acid such as p-hydroxybenzoic acid or β-hydroxynaphthoic acid with epichlorohydrin; polyglycidyl esters obtained by reacting a polycarboxylic acid such as phthalic acid or terephthalic acid with epichlorohydrin; glycidyl amine compounds obtained by reacting 4,4'-diaminodiphenyl methane, m-aminophenol or the like with epichlorohydrin; polyfunctional epoxy compounds such as an epoxidized phenol novolak resin, an epoxidized cresol novolak resin or epoxidized polyolefin; monofunctional epoxy compounds such as butyl glycidyl ether, phenyl glycidyl ether or glycidyl methacrylate; and the like. These may be used in combination.

The amines used in the production of the latent curing accelerator may be one having one or more active hydrogen atoms capable of performing an addition reaction with an epoxy group in the molecule and having at least one amino group selected from a primary amino group, a secondary amino group and a tertiary amino group in the molecule.

Examples of the amines include aliphatic amines such as diethylenetriamine, triethylenetetramine, n-propylamine, 2-hydroxyethylaminopropylamine, cyclohexylamine, and 4,4'-diaminodicyclohexylmethane, aromatic amine compounds such as 4,4'-diaminodiphenylmethane and o-methylaniline, nitrogen-containing heterocyclic compounds such as 2-ethyl-4-methylimidazole, 2-methylimidazole, 2-ethyl-4-methylimidazoline, 2,4-dimethylimidazoline, piperidine, and piperazine, and the like. These may be used in combination.

Of the amines described above, an amine having a tertiary amino group in the molecule provides a latent curing accelerator excellent in the cure-accelerating property.

Examples of such amines include aliphatic amines such as dimethylaminopropylamine, diethylaminopropylamine, di-n-propylaminopropylamine, dibutylaminopropylamine, dimethylaminoethylamine, diethylaminoethylamine, and N-methylpiperazine, imidazole compounds such as 2-methylimidazole, 2-ethylimidazole, 2-ethyl-4-methylimidazole, and 2-phenylimidazole, alcohols, phenols, thiols, carboxylic acids, hydrazides, each containing a tertiary amino group in the molecule, such as 2-dimethylaminoethanol, 1-methyl-2-dimethylaminoethanol, 1-phenoxymethyl-2-dimethylaminoethanol, 2-diethylaminoethanol, 1-butoxymethyl-2-dimethylaminoethanol, 1-(2-hydroxy-3-phenoxypropyl)-2-methylimidazole, 1-(2-hydroxy-3-phenoxypropyl)-2-ethyl-4-methylimidazole, 1-(2-hydroxy-3-butoxypropyl)-2-methylimidazole, 1-(2-hydroxy-3-butoxypropyl)-2-ethyl-4-methylimidazole, 1-(2-hydroxy-3-phenoxypropyl)-2-phenylimidazoline, 1-(2-hydroxy-3-butoxypropyl)-2-methylimidazoline, 2-(dimethylaminomethyl)phenol, 2,4,6-tris(dimethylaminomethyl)phenol, N-β-hydroxyethylmorpholine, 2-dimethylaminoethanethiol, 2-mercaptopyridine, 2-mercaptobenzimidazole, 2-mercaptobenzothiazole, 4-mercaptopyridine, N,N-dimethylaminobenzoic acid, N,N-dimethylglycine, nicotinic acid, isonicotinic acid, picolinic acid, N,N-dimethylglycine hydrazide, N,N-dimethylpropionic acid hydrazide, nicotinic acid hydrazide, and isonicotinic acid hydrazide, and the like. These may be used in combination.

In order to further improve storage stability of the epoxy resin composition according to the present invention, an active hydrogen compound having two or more active hydrogen atoms in the molecule may be added as a third component in the production of the latent curing accelerator.

Examples of the active hydrogen compound include polyhydric phenols such as bisphenol A, bisphenol F, bisphenol S, hydroquinone, catechol, resorcinol, pyrogallol, and phenol novolak resins, polyhydric alcohols such as trimethylolpropane, polybasic carboxylic acids such as adipic acid and phthalic acid, 1,2-dimercaptoethane, 2-mercaptoethanol, 1-mercapto-3-phenoxy-2-propanol, mercaptoacetic acid, anthranilic acid, lactic acid, and the like. These may be used in combination.

Examples of the isocyanate compound used as a surface treating agent in the production of the latent curing accelerator include monofunctional isocyanate compounds such as n-butyl isocyanate, isopropyl isocyanate, phenyl isocyanate, and benzyl isocyanate, and polyfunctional isocyanate compounds such as hexamethylene diisocyanate, toluylene diisocyanate, 1,5-naphthalene diisocyanate, diphenylmethane-4,4'-diisocyanate, isophorone diisocyanate, xylylene diisocyanate, p-phenylene diisocyanate, 1,3,6-hexamethylene triisocyanate, and bicycloheptane triisocyanate. These may be used in combination.

In place of the polyfunctional isocyanate compound, a terminal isocyanate group-containing compound obtained by a reaction of a polyfunctional isocyanate compound with an active hydrogen compound, may be used.

Examples of such a compound include a terminal isocyanate group-containing addition reaction product obtained by a reaction of toluylene diisocyanate with trimethylolpropane, a terminal isocyanate group-containing addition reaction product obtained by a reaction of toluylene diisocyanate with pentaerythritol, and the like. These may be used in combination.

The acidic compound used as a surface treating agent in the production of the latent curing accelerator may be in any form of gas, liquid and solid, and may be any of an inorganic acid and an organic acid.

Examples the acidic compound include carbon dioxide gas, sulfurous acid gas, sulfuric acid, hydrochloric acid, oxalic acid, phosphoric acid, acetic acid, formic acid, propionic acid, adipic acid, caproic acid, lactic acid, succinic acid, tartaric acid, sebacic acid, p-toluenesulfonic acid, salicylic acid, boric acid, tannic acid, alginic acid, polyacrylic acid, polymethacrylic acid, phenol, pyrogallol, phenol resins, resorcin resins, and the like. These may be used in combination.

The latent curing accelerator can be obtained by mixing an amine, an epoxy resin, and, if desired, an active hydrogen compound, reacting the mixture at temperature of from room temperature to 200° C., and solidifying and pulverizing the resulting product, or reacting the mixture in a solvent such as methyl ethyl ketone, dioxane or tetrahydrofuran, removing the solvent, and pulverizing the resulting solid component.

The content of the curing agent in the epoxy resin composition according to the present invention is preferably adjusted such that a proportion of the mercapto group present in the curing agent to the epoxy group present in the epoxy resin composition (proportion of SH equivalent number/epoxy equivalent number) is from 0.5 to 1.2.

In addition, the content of the latent curing accelerator is preferably adjusted to be from 0.1 to 10 parts by weight based on 100 parts by weight of the epoxy resin.

A commercially available product may be used as the latent curing accelerator. Examples thereof include commercially available products such as "Amicure PN-23" (trade name, Ajinomoto Fine-Techno Co., Inc.), "Amicure PN-H" (trade name, Ajinomoto Fine-Techno Co., Inc.), "Amicure MY-24" (trade name, Ajinomoto Fine-Techno Co., Inc.), "Novacure HX-3742" (trade name, Asahi Kasei Corp.), "Novacure HX-3721" (trade name, Asahi Kasei Corp.), and the like. These may be used in combination.

Incorporation of an isocyanate compound into the epoxy resin composition according to the present invention can improve the adhesive force of the cured product without impairing the curing properties of the epoxy resin composition.

Examples of such an isocyanate compound include n-butyl isocyanate, isopropyl isocyanate, 2-chloroethyl isocyanate, phenyl isocyanate, p-chlorophenyl isocyanate, benzyl isocyanate, hexamethylene diisocyanate, 2-ethylphenyl isocyanate, 2,6-dimethylphenyl isocyanate, 2,4-toluene diisocyanate, 2,6-toluene diisocyanate, 1,5-naphthalene diisocyanate, diphenylmethane-4,4'-diisocyanate, tolidine diisocyanate, isophorone diisocyanate, xylylene diisocyanate, p-phenylene diisocyanate, 1,3,6-hexamethylene triisocyanate, bicycloheptane triisocyanate, and the like. These may be used in combination.

The isocyanate compound is generally used in a ratio of from 0.1 to 20 parts by weight based on 100 parts by weight of the epoxy resin.

<(C) Regarding Use of Reaction Product of Isocyanate Compound and Compound Having Amino Group as Curing Accelerator>

In the epoxy resin composition according to the present invention, a reaction product of an isocyanate compound and a compound having an amino group may be used as the curing accelerator.

The reaction product can be obtained by allowing an isocyanate compound to react with a compound having a primary and/or secondary amino group in an organic solvent such as dichloromethane.

Examples of the isocyanate compound include n-butyl isocyanate, isopropyl isocyanate, 2-chloroethyl isocyanate, phenyl isocyanate, p-bromophenyl isocyanate, m-chlorophenyl isocyanate, o-chlorophenyl isocyanate, p-chlorophenyl isocyanate, 2,5-dichlorophenyl isocyanate, 3,4-dichlorophenyl isocyanate, 2,6-dimethylphenyl isocyanate, o-fluorophenyl isocyanate, p-fluorophenyl isocyanate, m-tolyl isocyanate, p-tolyl isocyanate, o-trifluoromethylphenyl isocyanate, m-trifluoromethylphenyl isocyanate, benzyl isocyanate, hexamethylene diisocyanate, 2,4-toluylene diisocyanate, 2,6-toluylene diisocyanate, 1,5-naphthalene diisocyanate, diphenylmethane-4,4'-diisocyanate, 2,2-dimethyldiphenylmethane-4,4'-diisocyanate, tolidine diisocyanate, isophorone diisocyanate, xylylene diisocyanate, 1,3-bis(isocyanatomethyl)cyclohexane, p-phenylene diisocyanate, 1,3,6-hexamethylene triisocyanate, bicycloheptane triisocyanate, tris(3-isocyanato-4-methylphenyl)isocyanurate, tris(6-isocyanatohexyl)isocyanurate, and the like. These may be used in combination.

Examples of the compound having a primary and/or secondary amino group include dimethylamine, diethylamine, di-n-propylamine, di-n-butylamine, di-n-hexylamine, di-n-octylamine, di-n-ethanolamine, dimethylaminopropylamine, diethylaminopropylamine, morpholine, piperidine, 2,6-dimethylpiperidine, 2,2,6,6-tetramethylpiperidine, piperazine, pyrrolidine, benzylamine, N-methylbenzylamine, cyclohexylamine, metaxylylenediamine, 1,3-bis(aminomethyl)cyclohexane, isophoronediamine, N-aminoethylpiperazine, 2-methylimidazole, 2-ethyl-4-methylimidazole, 2-undecylimidazole, 2-phenylimidazole, 1,1-dimethylhydrazine, and the like. These may be used in combination.

In the epoxy resin composition according to the present invention, the curing accelerator containing the reaction product of the isocyanate compound and the compound having an amino group as a component is used in a ratio of from 1 to 10 parts by weight based on 100 parts by weight of the epoxy resin.

The epoxy resin composition according to the present invention may contain, if desired, a filler, a diluent, a solvent, a flexibility imparting agent, a coupling agent, an antioxidant, a flow behavior controller such as silicic acid, magnesium silicate or barium sulfate, a thermal conductivity imparting agent such as alumina, a conductivity imparting agent such as silver or carbon, and a coloring agent such as a pigment or a dye.

The cured product obtained from the epoxy resin composition according to the present invention is excellent in hydrolysis resistance, heat resistance, moisture resistance, and the like, and thus the epoxy resin composition can be suitably used as a component for an adhesive or a sealing agent.

The production method of the epoxy resin composition according to the present invention is not particularly limited and it can be obtained by weighing the respective components described above in the predetermined amounts, mixing by stirring the components, and then mixing or melt kneading by using a roll kneader, a kneader, an extruder, or the like.

The curing method of the epoxy resin composition according to the present invention is not particularly limited, and a curing device such as a sealed curing furnace or a tunnel furnace capable of continuous curing can be employed. Also, there is no particular limitation as to the heating source, and a method of hot air circulation, infrared ray heating, high frequency heating or the like can be employed. The curing temperature and curing time may be appropriately set.

EXAMPLE

The present invention will be described in more detail with reference to Examples and Comparative Examples, but the invention should not be construed as being limited thereto.

Example 1

Production of 1,1'-(dithio-bisethanediyl)-bis[3,4,6-tris(2-mercaptoethyl)glycoluril]

Into a 30 mL flask equipped with a thermometer was put 3.18 g (10.0 mmol) of 1,3,4,6-tetrakis(2-hydroxyethyl)glycoluril, and 11.75 g (99.4 mmol) of thionyl chloride was added dropwise thereto with stirring at room temperature.

After completion of the dropwise addition, the mixture was stirred under reflux for 2 hours, cooled to 10° C., and 10 mL of water was added thereto. Subsequently, 3.65 g (48.0 mmol) of thiourea was added to the mixture, followed by stirring under reflux for 12 hours.

After completion of the reaction, the reaction mixture (reaction solution) was cooled to 25° C., and 4.00 g (48.0 mmol) of a 48% aqueous sodium hydroxide solution was added dropwise thereto under a nitrogen atmosphere, followed by stirring at 70° C. for 9 hours.

After completion of the reaction, the reaction mixture was cooled to 20° C., 3.50 g (35.0 mmol) of concentrated hydrochloric acid was added thereto, subsequently 10 mL of chloroform was added thereto, followed by stirring for 30 minutes, and subjected to a first suction filtration.

To the resulting filtration cake was added 10 mL of chloroform, and the mixture was stirred for 30 minutes and subjected to a second suction filtration. The filtrate obtained by the first suction filtration and the filtrate obtained by the second suction filtration were put together, the aqueous layer was removed. The remaining organic layer of the filtrate was washed 5 times with 5 mL of water, and then the aqueous layer was removed.

The resulting organic later was concentrated under a reduced pressure at 80° C. to obtain 3.25 g of a yellow oily product (crude product).

The crude product was purified by column chromatography (eluent: chloroform) to obtain 0.26 g of a pale yellow oily product (purified product) (yield: 7%).

$^1$H-NMR spectral data of the purified product were as follows:

$^1$H-NMR (CDCl$_3$) δ: 5.50-5.56 (m, 4H), 3.80-3.88 (m, 2H), 3.69-3.78 (m, 6H), 3.47-3.56 (m, 2H), 3.31-3.41 (m, 6H), 2.99-3.09 (m, 2H), 2.81-2.93 (m, 8H), 2.67-2.77 (m, 6H), 1.44-1.52 (m, 6H).

The IR spectral data of the purified product obtained was as shown in the chart shown in FIG. 1.

From these spectral data, the purified product obtained was identified as the subject glycoluril compound.

In addition, as a result of HPLC analysis of the crude product, it was confirmed that the crude product contained 1,3,4,6-tetrakis(2-mercaptoethyl)glycoluril as the main component and 8% by weight of 1,1'-(dithio-bisethanediyl)-bis[3,4,6-tris(2-mercaptoethyl)glycoluril].

Reference Example 1

Production of 1,3,4,6-tetrakis(2-mercaptoethyl)glycoluril

The crude product obtained in Example 1 was purified by column chromatography (eluent: chloroform/methanol=10:1) to obtain 2.90 g of 1,3,4,6-tetrakis(2-mercaptoethyl)glycoluril as white crystals (melting point: 75.3 to 77.8° C.).

Example 2

An epoxy resin composition was prepared by mixing 100 parts by weight of an epoxy resin ("jER 828" produced by Mitsubishi Chemical Corp.) with 56 parts by weight of 1,3,4,6-tetrakis(2-mercaptoethyl)glycoluril containing 1,1'-(dithio-bisethanediyl)-bis[3,4,6-tris(2-mercaptoethyl)glycoluril] of the crude product obtained in Example 1, as a curing agent.

This epoxy resin composition was allowed to stand at room temperature to measure time elapsing from the preparation of the epoxy resin composition to the time that the crystal deposition of 1,3,4,6-tetrakis(2-mercaptoethyl)glycoluril was confirmed. The confirmation of the crystal deposition was visually performed.

The measurement result obtained was as shown in Table 1.

Comparative Example 1

An epoxy resin composition was prepared in a similar manner with Example 2 by mixing 100 parts by weight of the epoxy resin and 56 parts by weight of 1,3,4,6-tetrakis(2-mercaptoethyl)glycoluril obtained in Reference Example 1, as a curing agent.

Subsequently, the time until the crystal deposition was confirmed in the epoxy resin composition obtained was measured in the same manner as in Example 2.

The measurement result obtained was as shown in Table 1.

TABLE 1

| | Example 2 | Comparative Example 1 |
|---|---|---|
| Curing Agent | 1,3,4,6-tetrakis(2-mercaptoethyl)glycoluril containing 1,1'-(dithio-bisethanediyl)-bis[3,4,6-tris(2-mercaptoethyl)glycoluril] | 1,3,4,6-tetrakis(2-mercaptoethyl)glycoluril |
| Time from Preparation of Composition to Confirmation of Crystal Deposition (hr) | 168 or more | 6 |

It is recognized that the epoxy resin composition containing, as a curing agent, 1,3,4,6-tetrakis(2-mercaptoethyl)glycoluril containing 1,1'-(dithio-bisethanediyl)-bis[3,4,6-tris(2-mercaptoethyl)glycoluril] is suppressed in the crystal deposition of 1,3,4,6-tetrakis(2-mercaptoethyl)glycoluril, in comparison with the epoxy resin composition containing, as a curing agent, 1,3,4,6-tetrakis(2-mercaptoethyl)glycoluril, when allowing to stand at room temperature.

Example 3

An epoxy resin composition was prepared by mixing 100 parts by weight of an epoxy resin ("jER 828" produced by Mitsubishi Chemical Corp.) with 56 parts by weight of 1,3,4,6-tetrakis(2-mercaptoethyl)glycoluril containing 1,1'-(dithio-bisethanediyl)-bis[3,4,6-tris(2-mercaptoethyl)glycoluril] of the crude product obtained in Example 1, as a curing agent, and 3 parts by weight of a solid dispersion-type amine adduct latent curing accelerator ("Amicure PN-23" produced by Ajinomoto Fine-Techno Co., Ltd.), as a curing accelerator.

This epoxy resin composition was heated at a temperature rising rate of 10° C./minute from 30° C. to 270° C. for curing, subsequently the cured product obtained was cooled at a temperature falling rate of −50° C./minute from 270° C. to 10° C., and then it was heated at a temperature rising rate of 10° C./minute from 10° C. to 100° C., whereby a glass transition temperature (Tg) of the cured product was measured.

The measurement of the glass transition temperature was performed by using a differential scanning calorimeter ("EXSTAR 6000" produced by SII Nano Technology Inc.).

The measurement result obtained was as shown in Table 2.

Comparative Example 2

An epoxy resin composition was prepared in the same manner as in Example 3 except for using 107 parts by weight of 1,3,5-tris(3-mercaptobutyryloxyethyl)-1,3,5-triazine-2,4,6(1H,3H,5H)-trione ("Karenz MT NR1" produced by Showa Denko K. K., hereinafter referred to as thiol compound (1)) in place of 56 parts by weight of 1,3,4,6-tetrakis(2-mercaptoethyl)glycoluril containing 1,1'-(dithio-bisethanediyl)-bis[3,4,6-tris(2-mercaptoethyl)glycoluril], as a curing agent, and glass transition temperature of the cured product of this epoxy resin composition was measured.

The measurement result obtained was as shown in Table 2.

The chemical structure of thiol compound (1) was shown by chemical formula (X).

[Chem. 7]

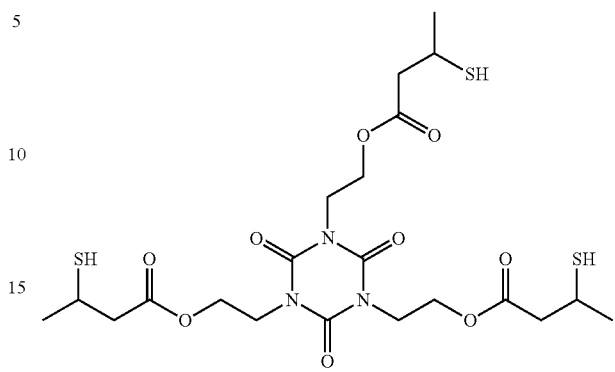

(X)

Comparative Example 3

An epoxy resin composition was prepared in the same manner as in Example 3 except for using 75 parts by weight of trimethylolpropane tris(3-mercaptopropionate) ("TMMP" produced by SC Organic Chemical Co., Ltd., hereinafter referred to as thiol compound (2)) in place of 56 parts by weight of 1,3,4,6-tetrakis(2-mercaptoethyl)glycoluril containing 1,1'-(dithio-bisethanediyl)-bis[3,4,6-tris(2-mercaptoethyl)glycoluril], as a curing agent, and glass transition temperature of the cured product of this epoxy resin composition was measured.

The measurement result obtained was as shown in Table 2.

The chemical structure of thiol compound (2) was shown by chemical formula (XI).

[Chem. 8]

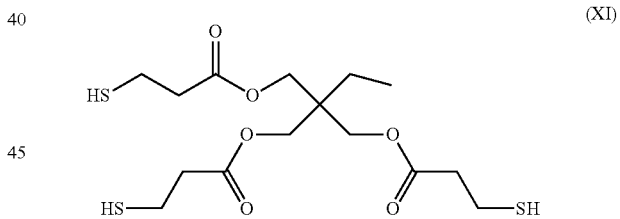

(XI)

TABLE 2

| | Example 3 | Comparative Example 2 | Comparative Example 3 |
|---|---|---|---|
| Curing Agent | 1,3,4,6-tetrakis(2-mercaptoethyl)glycoluril containing 1,1'-(dithio-bisethanediyl)-bis[3,4,6-tris(2-mercaptoethyl)glycoluril] | Thiol Compound (1) | Thiol Compound (2) |
| Tg of Cured Product (° C.) | 97 | 36 | 32 |

It is recognized that the cured product of the epoxy resin composition containing, as a curing agent, 1,3,4,6-tetrakis(2-mercaptoethyl)glycoluril containing 1,1'-(dithio-bisethanediyl)-bis[3,4,6-tris(2-mercaptoethyl)glycoluril] has high glass transition temperature and is excellent in the heat resistance, in comparison with the cured product of the epoxy resin composition containing, as a curing agent, thiol compound (1) or thiol compound (2).

Example 4

The epoxy resin composition prepared in Example 3 was applied to a blast-treated aluminum plate (A5052P, 100× 25×1.6 mm, produced by TP Giken Co., Ltd.) and cured under conditions of 80° C./60 minutes to produce a test piece.

For the test piece, the tensile shear bonding strength immediately after the production, and the tensile shear bonding strength after heating and humidification in a constant temperature and humidity chamber under conditions of 85° C./85% RH/1,000 hours were measured in accordance with JIS K 6850.

The test results obtained were as shown in Table 3.

Comparative Examples 4 and 5

With each of the epoxy resin compositions prepared in Comparative Examples 2 and 3, a test piece was produced in the same manner as in Example 4, and the tensile shear bonding strengths were measured.

The test results obtained were as shown in Table 3.

TABLE 3

| | | Example | Comparative Example | |
|---|---|---|---|---|
| | | 4 | 4 | 5 |
| Tensile Shear Bonding Strength (N/mm²) | Immediately after Production | 11.3 | 13.1 | 15.1 |
| | After Heating and Humidification (85° C./85% RH/1,000 hr) | 11 | 3.5 | 0.3 |

It is recognized that the cured product of the epoxy resin composition containing, as a curing agent, 1,3,4,6-tetrakis (2-mercaptoethyl)glycoluril containing 1,1'-(dithio-bisethanediyl)-bis[3,4,6-tris(2-mercaptoethyl)glycoluril] shows the tensile shear bonding strength after heating and humidification being not changed from the tensile shear bonding strength immediately after production (before heating and humidification) and thus, is excellent in the moisture resistance, in comparison with the cured products of the epoxy resin composition containing, as a curing agent, thiol compound (1) or thiol compound (2).

While the present invention has been described in detail and with reference to specific embodiments thereof, it will be apparent to those skilled in the art that various changes and modifications can be made therein without departing from the spirit and scope of the present invention.

This application is based on a Japanese patent application filed on Mar. 12, 2015 (Japanese Patent Application No. 2015-048959), and the entire contents thereof are incorporated herein by reference.

INDUSTRIAL APPLICABILITY

The epoxy resin composition containing an oligomer type mercaptoethylglycoluril compound and a monomer type mercaptoethylglycoluril compound as curing agents is suppressed in deposition of the monomer type mercaptoethylglycoluril compound and is excellent in stability for keeping uniform liquid state in comparison with the epoxy resin composition containing only the monomer type mercaptoethylglycoluril compound, so that it can be suitably used for applications such as adhesion, sealing, encapsulating, casting, molding, painting, and coating.

The invention claimed is:

1. A mercaptoethylglycoluril compound represented by chemical formula (I):

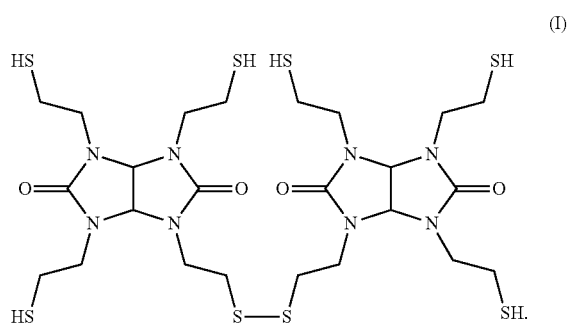 [SMILES: O=C1N(CCS)C2C(N1CCS)N(CCSSCCN1C(=O)N(CCS)C3C1N(CCS)C(=O)N3CCS)C(=O)N2CCS]

2. A curing agent for an epoxy resin, comprising a mercaptoethylglycoluril compound represented by chemical formula (I) and a mercaptoethylglycoluril compound represented by chemical formula (II)

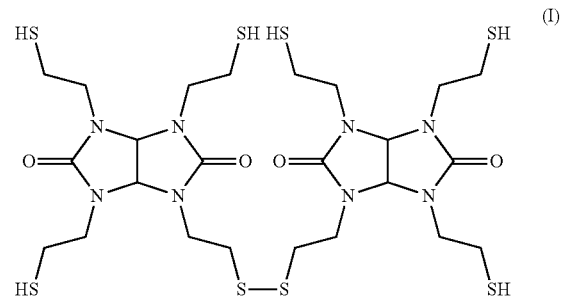

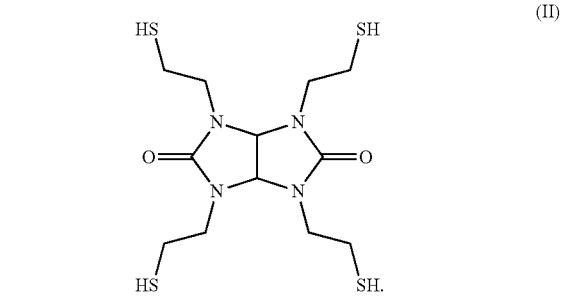

3. The curing agent for an epoxy resin according to claim 2, wherein the ratio of the content of the compound of formula (I) to the content of the compound of formula (II) is from 1 to 20% by weight.

4. A curing agent for an epoxy resin comprising (i) a mercaptoethylglycoluril compound represented by chemical formula (I), (ii) a mercaptoethylglycoluril compound represented by chemical formula (II), and (iii) optionally one or more oligomers selected from the compounds represented by chemical formulas (VI)-(IX):

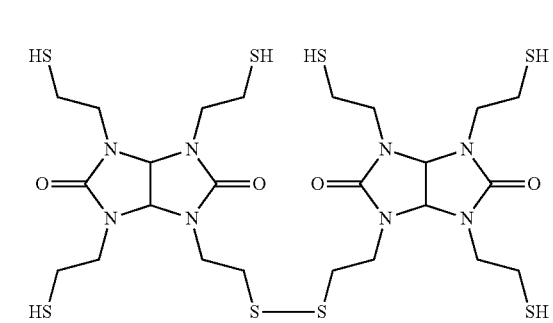
(I)
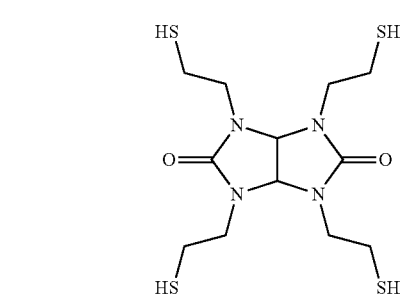
(II)
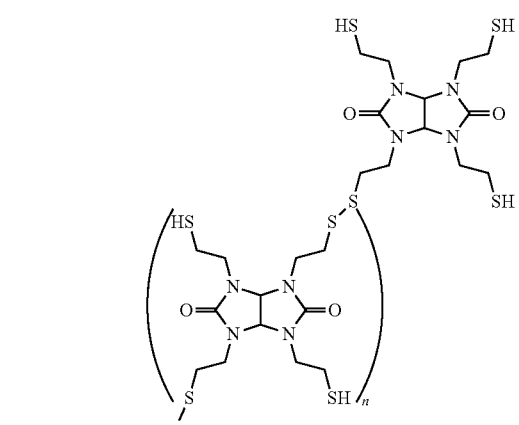
(VI)
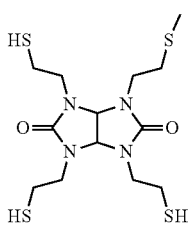
wherein in chemical formula (VI), n is 1, 2 or 3,
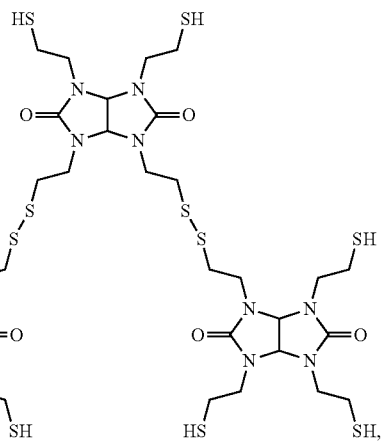
(VII)
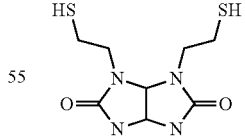
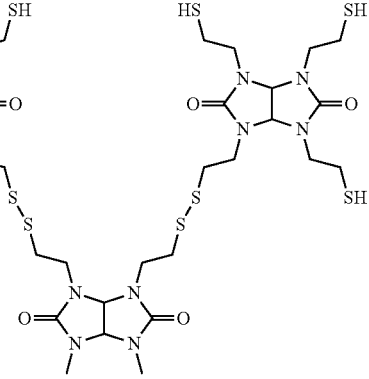
(IX)

-continued

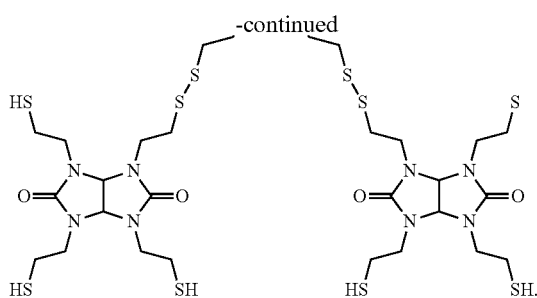

5. The curing agent for an epoxy resin according to claim 4, wherein the ratio of the combined content of compounds of formulas (I) and (VI)-(IX) to the content of the mercaptoethylglycoluril compound represented by chemical formula (II) is from 1 to 20% by weight.

6. An epoxy resin composition comprising the curing agent for an epoxy resin as described in claim 5 and an epoxy resin.

7. The epoxy resin composition according to claim 6, further comprising an amine as a curing accelerator.

8. The epoxy resin composition according to claim 6, further comprising a reaction product of an amine and an epoxy resin as a curing accelerator.

9. The epoxy resin composition according to claim 6, further comprising a reaction product of an isocyanate compound and a compound having an amino group, as a curing accelerator.

10. An epoxy resin composition comprising the curing agent for an epoxy resin as described in claim 4 and an epoxy resin.

11. The epoxy resin composition according to claim 10, further comprising an amine as a curing accelerator.

12. An adhesive comprising the epoxy resin composition as described in claim 5 as a component.

13. A sealing agent comprising the epoxy resin composition as described in claim 11 as a component.

14. The epoxy resin composition according to claim 10, further comprising a reaction product of an amine and an epoxy resin as a curing accelerator.

15. An adhesive comprising the epoxy resin composition as described in claim 14 as a component.

16. A sealing agent comprising the epoxy resin composition as described in claim 14 as a component.

17. The epoxy resin composition according to claim 10, further comprising a reaction product of an isocyanate compound and a compound having an amino group, as a curing accelerator.

18. An adhesive comprising the epoxy resin composition as described in claim 17 as a component.

19. A sealing agent comprising the epoxy resin composition as described in claim 17 as a component.

20. An adhesive comprising the epoxy resin composition as described in claim 10 as a component.

21. A sealing agent comprising the epoxy resin composition as described in claim 10 as a component.

* * * * *